(12) United States Patent
Tsabari et al.

(10) Patent No.: US 9,603,994 B2
(45) Date of Patent: Mar. 28, 2017

(54) DEVICE FOR ADMINISTERING LIQUIDS INTO AN ANIMAL BODY, IN PARTICULAR FOR ADMINISTERING THERAPEUTIC AGENTS VIA ENDOVASCULAR INFUSION

(75) Inventors: Shahar Tsabari, Tignale (IT); Carla Emilia Pace, Tignale (IT)

(73) Assignee: Shahar Tsabari, Tignale (bs) (IT)

( * ) Notice: Subject to any disclaimer, the term of this patent is extended or adjusted under 35 U.S.C. 154(b) by 1062 days.

(21) Appl. No.: 13/582,095

(22) PCT Filed: Mar. 4, 2011

(86) PCT No.: PCT/IB2011/050930
§ 371 (c)(1),
(2), (4) Date: Aug. 31, 2012

(87) PCT Pub. No.: WO2011/107969
PCT Pub. Date: Sep. 9, 2011

(65) Prior Publication Data
US 2012/0330279 A1    Dec. 27, 2012

(30) Foreign Application Priority Data
Mar. 5, 2010 (IT) .............................. PD2010A0066

(51) Int. Cl.
*A61M 5/14* (2006.01)
*A61M 5/168* (2006.01)

(52) U.S. Cl.
CPC ......... *A61M 5/1411* (2013.01); *A61M 5/1684* (2013.01); *A61M 2202/049* (2013.01)

(58) Field of Classification Search
CPC .... A61M 5/1411; A61M 5/1684; A61M 5/40; A61M 2205/3337; A61M 5/14;
(Continued)

(56) References Cited

U.S. PATENT DOCUMENTS

| 1,111,588 | A | * | 9/1914 | Iversen | ................ A61M 5/1411 604/122 |
|---|---|---|---|---|---|
| 3,722,529 | A | | 3/1973 | Arakawa | |
| 4,863,437 | A | * | 9/1989 | Clarke | ................ A61M 5/1411 137/843 |

FOREIGN PATENT DOCUMENTS

| EP | 1 535 641 | 6/2005 |
|---|---|---|
| FR | 2 555 520 | 5/1985 |

(Continued)

OTHER PUBLICATIONS

International Search Report of PCT/IB2011/050930, Aug. 26, 2011.

*Primary Examiner* — Bradley Osinski
(74) *Attorney, Agent, or Firm* — Collard & Roe, P.C.

(57) ABSTRACT

A device for administering liquids to an animal, in particular therapeutic agents, comprises a vessel (10; 50; 70; 100; 200) defining a collection chamber (11) therein. The following components are provided on the vessel: an inlet opening (13) for the therapeutic agent into the collection chamber, a first outlet duct (14) connected to a cannula element (3) which is prearranged so as to be introduced into the animal, the opening (14a) of the first outlet duct into the collection chamber being provided at a distance from a base (16) of the vessel, a second outlet duct (15) connected to a cannula element (3) which is prearranged so as to be introduced into the animal, the opening (15a) of the second outlet duct being provided substantially at the base of the vessel, and first shut-off means (17) for selectively shutting off the second outlet duct (15), the means being provided for preventing or allowing the flow from the collection chamber through the second outlet duct.

23 Claims, 6 Drawing Sheets

(58) Field of Classification Search
CPC .............. A61M 5/1407; A61M 5/1582; A61M 5/16818; A61M 5/16881
See application file for complete search history.

(56) References Cited

FOREIGN PATENT DOCUMENTS

| | | |
|---|---|---|
| JP | S63-177865 A | 7/1988 |
| JP | 09-056817 A | 3/1997 |
| JP | 2003-116986 A | 4/2003 |
| JP | 2006-280775 A | 10/2006 |
| JP | 3135582 U | 8/2007 |
| JP | 2008-036327 A | 2/2008 |

* cited by examiner

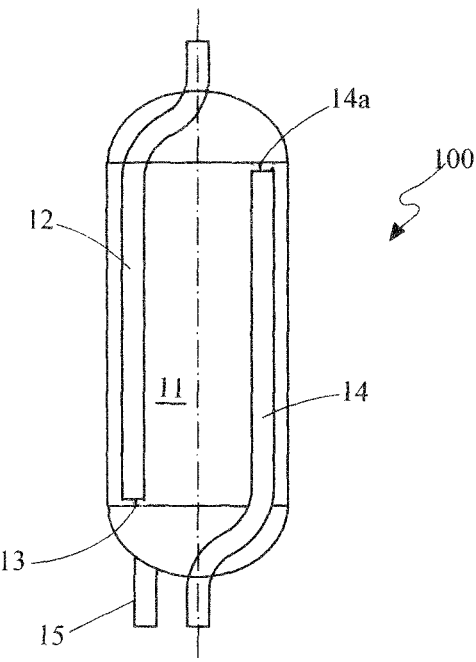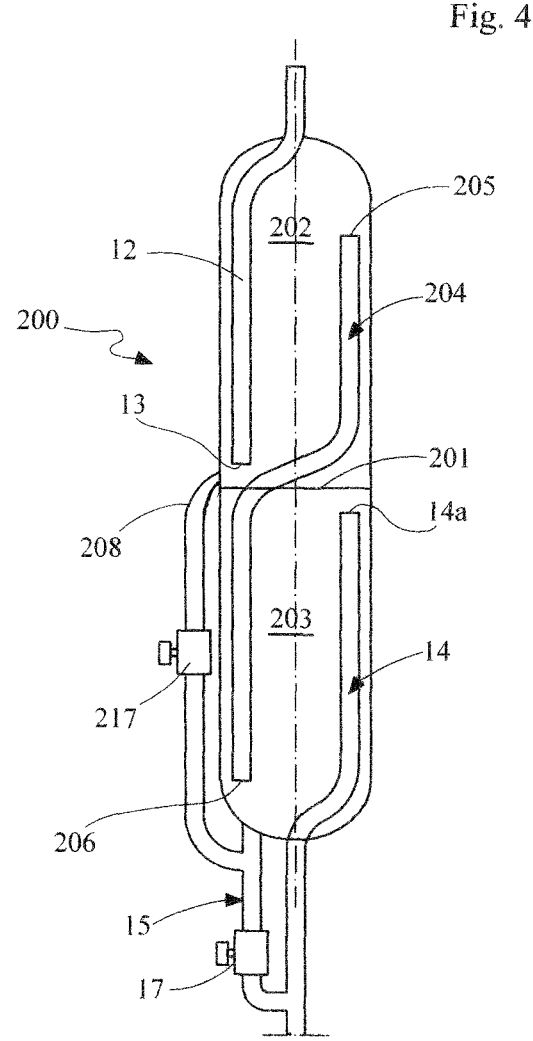

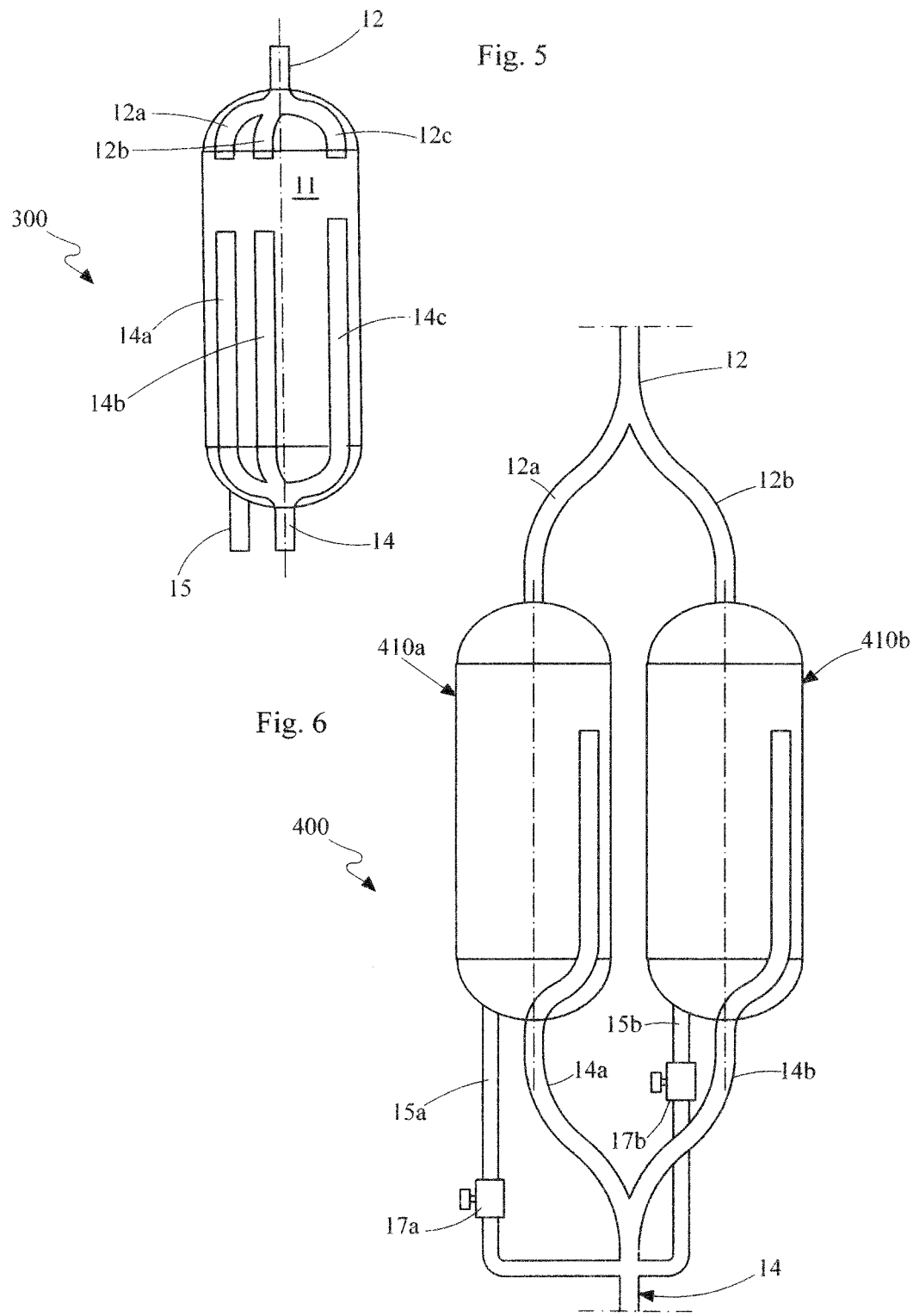

DEVICE FOR ADMINISTERING LIQUIDS INTO AN ANIMAL BODY, IN PARTICULAR FOR ADMINISTERING THERAPEUTIC AGENTS VIA ENDOVASCULAR INFUSION

CROSS REFERENCE TO RELATED APPLICATIONS

This application is the National Stage of PCT/IB2011/050930 filed on Mar. 4, 2011, which claims priority under 35 U.S.C. §119 of Italian Application No. PD2010A000066 filed on Mar. 5, 2010, the disclosure of which is incorporated by reference. The international application under PCT article 21(2) was published in English.

TECHNICAL FIELD

The present invention relates to a device for administering liquids to an animal body, in particular for administering therapeutic agents via endovascular infusion, said device having the features disclosed in the preamble of the main claim.

TECHNICAL BACKGROUND

The present invention can be used in particular, although not exclusively, in the administration within the medical or veterinary field of therapeutic agents by endovascular, typically endovenous, route.

It is known that some therapeutic agents are highly toxic to the human or animal organism. This is the case, in particular, with many drugs which are commonly used to treat tumoral pathologies, where the cytotoxicity of the therapeutic agents is itself the main characteristic used against the neoplastic formations.

Significant examples of cytotoxic therapeutic agents are given by compounds of the family of anthracyclines, vinca alkaloids, aminoanthraquinones, alkylating agents, pyrimidine analogues, non-anthracycline antibiotics, aziridines, platinum compounds, dialkyltriazenes, topoisomerase inhibitors, nitrosoureas, taxanes, etc.

Such therapeutic agents are generally administered by endovenous route and, owing to their cytotoxicity, may severely and irreversibly damage the body tissues with which they come into contact. For example, severe effects of sclerosis and necrosis of the veins used for infusion of the drug into the human body are known, which could lead to undesired extravasation of the therapeutic agent with subsequent extension of the damage to the surrounding tissues and organs. It should also be noted that extravasation, as well as being caused by iatrogenic vessel damage, can also be caused by vessel damage originating from other pathologies and/or as a result of haematic flow altered by surgical interventions, by radiotherapy, or by an error on the part of a healthcare professional, or by accidents during the various phases of therapeutic administration, as a result of which the risk associated with the administration of cytotoxic therapeutic agents by endovenous route remains high.

In order to prevent or at least minimise the occurrence of damage to blood vessels which are directly concerned with the infusion of the drug, it would be necessary to administer the therapeutic agent with a flow rate which is low enough to keep the concentration of the drug in the blood below a defined danger threshold which varies from drug to drug. However, the administration protocols demand a maximum time within which the drug must be administered, which consequently imposes a minimum flow rate for endovascular infusion.

Unfortunately, in many cases, observation of the minimum flow rate means exceeding the danger threshold of the concentration of the drug, with subsequent damage of the blood vessel in question, particularly from the point of injection of the therapeutic agent over a subsequent stretch along the direction of the blood flow.

In everyday medical practice, such therapeutic agents are administered by drip by connecting an intravenous drip tube to a bottle containing the drug and to a needle introduced into a patient's vein. Conventional drips comprise a drip chamber, into which open an inlet duct which is connected to the bottle and an outlet duct which opens into the base of the drip chamber and is connected to the needle. The inlet duct is of such a size that the drug enters the drip chamber dropwise, in such a way that correct operation of the device can be checked. Furthermore, a flow regulator is normally provided on the outlet duct in order to reduce or increase the flow rate of the therapeutic agent.

A possible alternative solution for keeping the concentration of the drug below the danger threshold whilst observing the administration time provides dilution of the drug, for example with physiological solution, while keeping the specific flow rate of the drug constant. However, this would make it necessary to administer a greater amount of liquid both per unit of time and overall, increasing (possibly significantly) the amount of blood in circulation and altering the concentration values of the blood cells.

This possible solution is therefore also difficult to implement in practice.

Furthermore the drug cannot be excessively diluted, because there would be a risk of nullifying the obtainable therapeutic effect and excessively altering the plasma volume and blood pressure of the patient, and the maximum possible dilution is not sufficient to prevent the aforementioned damage to the blood vessels.

EP 1535641 discloses a device for the administration of drugs to a patient, comprising a vessel, into the top of which an inlet duct opens, an outlet duct which opens into the base of the vessel and is prearranged so as to be placed in communication with the body of the patient, and a third duct which opens into the top of the vessel and opens outwardly, in such a way that air can pass from and to the interior of the vessel in a controlled manner.

DESCRIPTION OF THE INVENTION

The problem behind the present invention is to provide a device for administering a liquid, in particular a therapeutic agent, to an animal body, which device is structurally and functionally designed so as to overcome the limitations mentioned above with reference to the cited known prior art.

Based on this problem, an object of the invention is to provide a device which is economical, of simple construction and can be applied immediately. This problem is solved and this object is achieved by the present invention by a device for administering a liquid to an animal, which device is formed in accordance with the claims below.

BRIEF DESCRIPTION OF THE DRAWINGS

The features and advantages of the invention will become clearer from the detailed description of some of the embodiments of the invention, which are provided purely by way of non-limiting example and with reference to the appended drawings, in which:

FIGS. 2a, 2b and 3 to 6 are schematic enlarged views of respective further possible variants of the component of FIG. 2;

PREFERRED EMBODIMENTS OF THE INVENTION

Figure 1:
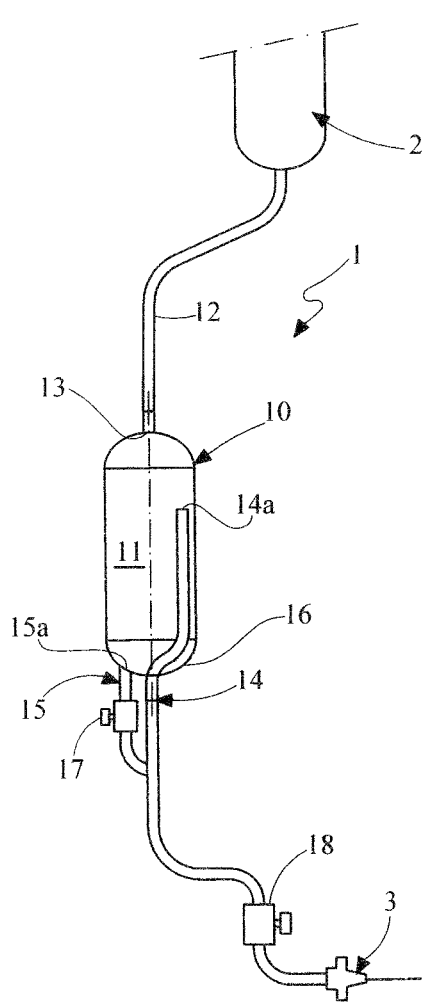
FIG. 1 is a schematic view of a device for administering a therapeutic agent formed in accordance with the present invention.
Figure 2:
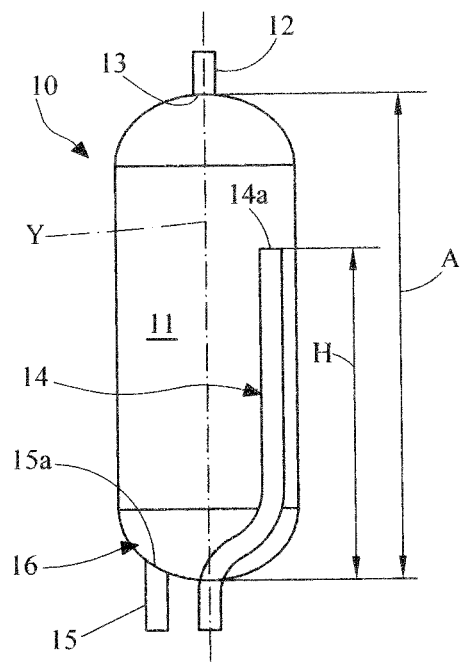
FIG. 2 is a schematic enlarged view of a component of the device of FIG. 1.

With initial reference to FIGS. 1 and 2, reference numeral 1 denotes, as a whole, a device for administering a liquid to an animal, in particular a therapeutic agent, which device is formed in accordance with the present invention.

The device 1 is typically used for administration by drip, for which purpose the device is connected on one side to a bottle 2 containing a therapeutic agent to be administered to a patient and comprises, on the other side, a cannula element which is prearranged so as to be introduced into a blood vessel of the patient, for example a vein.

In the preferred embodiment described here, the cannula element is represented by a needle 3, but it is noted that this could be formed analogously, for example, by a catheter.

It should be noted that, as in all applications by drip, the therapeutic agent is infused via the device 1 by falling downwards, for which purpose, under conditions of correct usage, the bottle 2 is placed at a substantially greater height than the point of insertion of the needle 3 in the patient.

Of course the device 1 can be connected to a pump or other means adapted for the supply of liquids to be introduced into a human or animal patient, instead of to the drip bottle 2.

In the present description, so as to be identified unambiguously, whenever the terms 'above' and 'below' are used they refer to components of the device 1 when positioned under conditions of correct use.

The device 1 comprises a vessel 10 defining a collection chamber 11 therein, which vessel is connected to the bottle 2 by an inlet duct 12 and to the needle 3 by a first outlet duct 14.

The inlet duct 12 leads into the collection chamber 11 at an inlet opening 13 which is formed in a top portion of the vessel 10, whereas the first outlet duct 14 has an opening 14a inside the collection chamber 11, which opening is advantageously prearranged in a position which is raised from a base 16 of the vessel 10. In particular, the opening 14a of the first outlet duct 14 is positioned at a height H relative to the base 16 representing at least 20% of the total height A of the vessel 10 and preferably at least 50% of the total height A of the vessel 10.

The height H at which the opening 14a of the first outlet duct 14 is positioned defines a fill level of the collection chamber 11 which must be reached by the liquid present therein before said liquid flows inside the first duct 14.

The height H is preferably determined in such a way that the volume defined between the base 16 and the fill level corresponding to the opening 14a of the first outlet duct 14 is between 50 and 500 ml. The person skilled in the art will, from time to time, be able to assess the volume which is most suitable for use as a function of the amount, the chemical-physical properties and the maximum concentration of the therapeutic agent to be administered, and as a function of the patient (human or animal) to which such an agent must be administered.

The opening 14a of the first outlet duct is advantageously offset relative to the vertical Y passing through the inlet opening 13, in such a way that the therapeutic agent entering the collection chamber 11 does not enter the first outlet duct 14 directly.

In a preferred embodiment the first outlet duct 14 extends inside the collection chamber 11 in the vicinity of a wall of the vessel 10, and the opening 14a is formed at the top thereof.

In a variant which is not shown it is provided for the inlet duct 12 to project slightly inside the collection chamber 11, in such a way that the inlet opening 13 is not formed directly in the top wall of the vessel 10. The dripping of the therapeutic agent entering the collection chamber 11 is thus ensured, even if the vessel 10 is in a position which is inclined relative to the vertical.

In a variant which is not shown it is further provided for the first outlet duct 14 to extend outside the vessel 10, and for its opening 14a inside the collection chamber 11 to be formed in a side wall of the vessel 10.

A second outlet duct 15 having an opening 15a inside the collection chamber 11 prearranged substantially at the base 16 is also provided on the vessel 10.

A valve 17 is further provided on the second outlet duct 15 and forms first selective shut-off means of said duct, and makes it possible to prevent or allow the flow from the collection chamber 11 through the second outlet duct 15.

The valve 17 may be of any suitable type as long as it is adapted to allow all or to prevent the flow of liquid through the second outlet duct 15. It can therefore be of the automatic, manual or remote-control type, applied directly on the duct or at the entry thereof inside the vessel, or may be a floating valve, a spring valve, a magnetic valve, etc.

The second outlet duct 15, with a Y-shaped connection, preferably merges into the first outlet duct 14 downstream of the valve 17 in such a way that said second outlet duct is also connected to the needle 3.

A flow regulator 18 is provided on a portion of the outlet duct positioned downstream of the merging of the second outlet duct 15 in order to control, interrupt or activate the flow to the needle 3.

The device 1 may further be equipped with one or more air intakes, filters, control sensors (for example pressure, flow, leakage or air sensors) and other accessories depending on the functions and aims required by the application in question.

The administration of a therapeutic agent by the device 1 is achieved in accordance with the following procedures.

The first outlet duct 14 is connected to the needle 3 which has previously been inserted into a patient's blood vessel, for example into a vein in an arm. The valve 17 is kept closed. A predetermined amount of the patient's blood is sucked inside the collection chamber 11 through the first outlet duct 14.

The vessel 1 can be de-pressurised in order to facilitate the aforementioned suction process.

Before the suction process, the vessel 10 may optionally be sterilised, radiated, chemically treated, or pre-medicated in various ways so as to render it suitable and ready to contain liquids to be introduced into the body of a patient.

The inlet duct 12 is then connected to the bottle 2 and the therapeutic agent begins to flow, by dripping, into the collection chamber 11 through the inlet opening 13.

The therapeutic agent is introduced into the first outlet duct 14 only once it has been mixed with the blood present in the collection chamber 11 and, of course, once the blood/therapeutic agent mixture has if necessary reached the corresponding level of the opening 14a.

The predetermined amount of blood introduced into the collection chamber 11 before the entry of the therapeutic agent into said collection chamber is determined as a function of the maximum concentration of therapeutic agent which can be introduced into the vein of the patient without damaging it. In other words, this amount of blood represents the necessary volume which must be pre-mixed with the therapeutic agent in order to obtain the desired concentration of the therapeutic agent during the entire course of administration.

The vessel 10 is preferably of such a size that the predetermined amount of blood introduced into the collection chamber 11 reaches a level which is below the level of the opening 14a. It is thus necessary, before the blood/therapeutic agent mixture is introduced into the first outlet duct 14, for at least some of the therapeutic agent to have been introduced into the collection chamber 11 and therefore to have been adequately mixed with the blood during the time spent inside the collection chamber.

Once the therapeutic agent has been supplied, typically once the bottle 2 has been emptied, some of the blood and therapeutic agent mixture remains in the collection chamber 11 and fills the entire volume defined between the base 16 and the level of the opening 14a.

At this point the valve 17 is opened in such a way that it allows the collection chamber 11 to be emptied via the second duct 15 which, for this purpose, has its opening 15a arranged in the base 16.

Once the vessel 10 has been emptied, it is possible to continue with a new administration of drug, or else with a washing procedure, for example using physiological solution, simply by substituting the bottle 2 with another bottle.

It is alternatively provided for the bottle of physiological solution to be connected directly to the inlet duct 12 by a separate duct equipped with a shut-off valve.

Figure 2A:
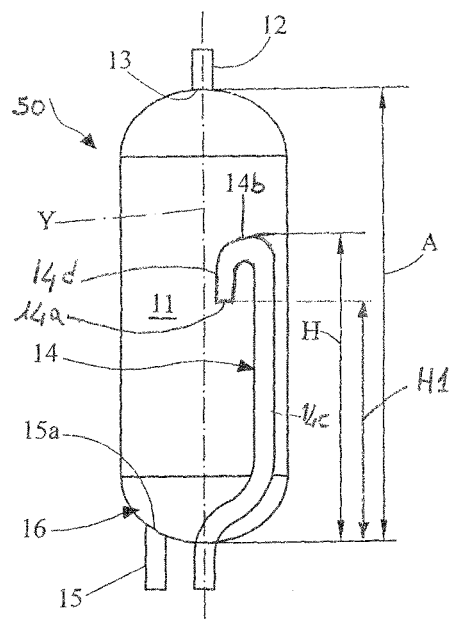

FIG. 2a shows a first variant of the vessel 10, denoted as a whole by 50, in which components corresponding to the example above are denoted by like reference numerals.

In the vessel 50, the end of the first outlet duct 14 in which the opening 14a is formed is curved towards the base 16 of the vessel, in such a way that the opening 14a is arranged at a level H1 below a curve of maximum height 14b which connects the ascending branch 14c to the descending branch 14d of the first outlet duct 14.

In this case, the fill level H which must be reached by the liquid in the collection chamber 11 before said liquid exits through the first outlet duct 14 no longer corresponds to the level of the opening 14a, but instead to the level of the curve of maximum height 14b.

As a result of this provision, the liquid which is administered to the patient through the first outlet duct 14 is that present at the level H1, that is to say at a depth from the surface of the liquid present in the collection chamber 11 equal to (H-H1). This provision is particularly advantageous in cases in which the therapeutic agent to be administered is less dense than blood and therefore tends to diffuse with some difficulty from the surface of the partially mixed liquid to the base. In fact, in these cases the difference in density may give rise to the formation of a superficial layer with a prevalent concentration of therapeutic agent, a base layer which is prevalently formed by blood, and a layer of intermediate diffusion in which the mixture of blood and therapeutic agent is more homogeneous. The special configuration of the first outlet duct 14 of this embodiment is specifically designed to draw from the layer of intermediate diffusion.

The mode of use of the device with the vessel 50 is basically the same as that described above with reference to the device 1.

Figure 2B:
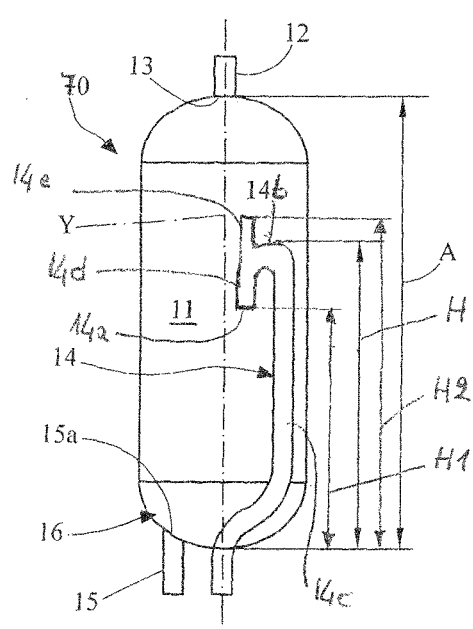

FIG. 2b shows a second embodiment of the vessel 10, denoted as a whole by 70, in which components which are similar to the example above are denoted by like reference numerals.

The first outlet duct 14 of the vessel and 70 differs from the corresponding first outlet duct of the vessel 50 illustrated in FIG. 2a in that it also has, in addition to the opening 14a which is turned towards the base 16, upstream of the curve of maximum height 14b and at the descending branch 14d of the first outlet duct 14, a vent 14e which extends vertically upwards relative to the opening 14a and opens, inside the collection chamber 11, at a level H2 above the level H of the curve of maximum height 14b.

Use of the vessel 70 is particularly advantageous in the situations indicated above with reference to the vessel 50, with regard to which the following further advantages are afforded owing to the provisions described above. Firstly, any undesired occurrences of suction by capillarity of the liquid present in the collection chamber 11 through the first outlet duct 14 are avoided since the vent 14e interrupts the fluid fillet which may be generated.

Furthermore, any air bubbles entering through the opening 14a are discharged via the vent 14e.

FIG. 3 shows a third variant of the vessel 10, denoted as a whole by 100, in which components corresponding to the example above are denoted by like reference numerals.

In the vessel 100 the opening 13 of the inlet duct 12 is not prearranged at the top of the vessel, as in the example above, but is positioned at a level below the opening 14a of the first outlet duct 14. This can be achieved by introducing the inlet duct 12 through the side wall or base 16 of the vessel 100, or else, as in the preferred example illustrated in FIG. 3, by extending the inlet duct 12 inside the collection chamber 11 from the top of the vessel 100 along a side wall of said collection chamber.

The inlet duct 12 can extend over any length deemed suitable, for example it can reach close to the base 16 or else as far as a middle region of the vessel 100, provided however that its opening 13 is arranged at a level below the opening 14a.

The inlet duct 12 preferably extends inside the collection chamber 11 opposite the first outlet duct 14. By using the vessel 100 it is advantageously possible to obtain very effective and homogeneous mixing of the therapeutic agent introduced through the inlet duct 12 and of the blood (or the blood-therapeutic agent mixture) present in the collection chamber 11 before being introduced into the first outlet duct 14 and being administered to the patient.

However, in this way, it is no longer possible to observe the drops which enter the vessel 100, and it is therefore expedient to provide a separate drip chamber which is arranged, for example, on the inlet duct 12. Furthermore, in order to obtain the above-mentioned positive mixing effects, it will be expedient to use the device 100 to administer drugs having a density which is not too much greater than that of the blood in which they are to be mixed.

FIG. 4 shows a fourth embodiment of the vessel 10, denoted as a whole by 200, in which components corresponding to the examples above are denoted by like reference numerals.

The vessel 200 is particularly configured to achieve effective mixing between therapeutic agent and blood present in the collection chamber by providing of two mixing processes in succession.

In fact, the collection chamber 11 of the vessel 200 is divided by a partitioning wall 201 into a first compartment 202, in which the opening of the inlet 13 is provided, and a second compartment 203, into which the first and second outlet ducts 14 and 15 open.

The second compartment 203 is arranged in cascade below the first compartment 202 and is in fluid communication therewith via a connecting duct 204 which extends through the partitioning wall 201 and opens out into both of the compartments 202, 203 at respective openings 205 and 206.

The opening 205 of the connecting duct 204 preferably opens into the first compartment 202 at a level above the inlet opening 13, which may for example be formed at the lower free end of an inlet duct 12 which extends as far as the vicinity of the partitioning wall 201.

Similarly, it is preferably provided for the opening 206 of the connecting duct 204 to be formed in the second compartment 203 at a level below the opening 14a of the first outlet duct 14, which may conveniently extend as far as the vicinity of the partitioning wall 201.

In order to improve the mixing effect, it is provided for the connecting duct 204 to extend inside the compartments 202 and 203 opposite the inlet duct 12 and the first outlet duct 14 respectively.

In order to make it possible to empty the first compartment 202, a third outlet duct 208 is provided at the base of said first compartment defined by the partitioning wall 201.

The third outlet duct 208 is equipped with second shut-off means 217, which are for example similar to the valve 17, and can then be connected to the first outlet duct 14 or to the second outlet duct 15, particularly preferably upstream of the valve 17, or else to the portion of the connecting duct 204 extending in the second compartment 203.

As mentioned above, the use of the vessel 200 makes it possible to improve the mixing effect obtained, and in fact the therapeutic agent, before exiting through the first outlet duct 14, is subjected to a first mixing process in the first compartment 202 and then to a second mixing process in the second compartment 203.

Once the therapeutic agent originating from the bottle 2 has been introduced, the collection chamber 11 is preferably emptied by opening, in a first step, the second shut-off means 217 of the third outlet duct 208 so as to empty the first compartment 202, and then by opening the first shut-off means 17 of the second outlet duct 15 so as also to empty the second compartment 203.

The case in which the third outlet duct 208 is connected to the second outlet duct 15 upstream of the first shut-off means 17 is the preferred embodiment, since the mixture present in the first compartment 202 is thus also introduced into the second compartment 203 via the second outlet duct 15.

Although in the example described and illustrated in this instance the collection chamber is divided into two compartments, it will be clear to the person skilled in the art how it is possible to produce vessels which are divided into three or more compartments which are in communication with one another in an appropriate manner.

Depending on the density of the therapeutic agent to the infused and/or of the patient's blood, or else depending on the chemical-physical properties of the therapeutic agent to be infused (pH, osmolarity, etc.), it is possible to select the variant of the administration device according to the invention which is most adapted to obtain optimum mixing of the therapeutic agent with the blood.

In order to further improve the mixing of the therapeutic agent with the blood, the end of the inlet duct 12 where the inlet opening 13 is defined can be configured similarly to a shower head or in a branched manner in order to form a multi-point inlet and increase the contact area between the two different liquids at the time of mixing inside the collection chamber 11. The same considerations also apply to the openings in the first outlet duct 14. This variant is advantageously reproducible both in the vessel 10 and in the vessel 100 and, in the case of the vessel 200, can also be applied to the inlet and outlet of the connecting duct 204.

Merely by way of example, FIG. 5 shows a vessel 300 in which both the inlet duct 12 and the first outlet duct 14 are divided into three branches denoted respectively as 12a-12c and 14a-14c, each of which opens into the collection chamber 11.

Meanwhile FIG. 6 schematically shows a device 400 in which two vessels 410a and 410b are present which are substantially similar to the vessel 10 of the first embodiment described above and are interconnected in parallel. In this case, the inlet duct 12 branches into two ducts 12a and 12b which open respectively into the two vessels 410a and 410b, and the first outlet duct 14 connects the liquid which has exited said vessels via two ducts 14a and 14b.

Similarly, each vessel 410a, 410b is equipped with a second outlet duct 15a, 15b which is equipped with first shut-off means 17a, 17b and then flows into the first outlet duct 14.

The present invention thus solves the problem described above with reference to the cited known prior art, whilst simultaneously offering a number of further advantages, including the fact that it provides significantly reduced production costs and does not complicate conventional drip operation.

Furthermore, the use of the device according to the invention makes it possible to administer a suitably diluted therapeutic agent to a patient via a drip without increasing either the overall administration time of the drug or the amount of liquid introduced into the patient's circulatory system (except, of course, the liquid relating to the therapeutic agent).

As mentioned above, the device according to the present invention is preferably used in the administration of cytotoxic therapeutic agents which could cause, if introduced in their natural state, damage to the patient's blood vessels or to adjacent tissues in the case of extravasation of various origins. Examples of therapeutic agents of this type are listed below. Oncological chemotherapy agents which are phlogogenic, irritant, exfoliant, vesicant and necrotising:

anthracyclines: epirubicin, aclarubicin, adriamycin, daunorubicin;
vinca alkaloids: vinblastine, vincristine, vindesine, vinorelbine;
aminoanthraquinones: mitoxantrone;
alkylating agents: mechlorethamine, mustine, treosulphan;
pyrimidine analogues: floxuridine;
non-anthracycline antibiotics: actinomycin D;
aziridines: mitomycin C;
platinum compounds: cisplatin, oxaliplatin;

dialkyltriazenes: dacarbazine;
topoisomerase inhibitors: topotecan;
nitrosoureas: carmustine, streptozocin;
taxanes: docetaxel, paclitaxel, taxol, taxotere.

Families of oncological chemotherapy drugs which are phlogogenic and irritant:
alkylating agents: cyclophosphamide, oestramustine, ifosfamide, melphalan;
pyrimidine analogues: 5-fluorouracil;
non-anthracycline antibiotics: bleomycin;
antimetabolites: methotrexate;
platinum compounds: carboplatin;
epipodophyllotoxins: etoposide, teniposide;
topoisomerase inhibitors: irinotecan;
aziridine polyalkylating agents: thiotepa.

Families of cardiovascular drugs which are phlogogenic and irritant:
antiarrhythmics: amiodarone;
sympathomimetic amines: dobutamine, dopamine.

Families of antibiotic drugs which are phlogogenic and irritant:
am inoglycosides: am ikacin;
b-lactams: nafcillin;
polyenes and antimycotics: amphotericin B.

Families of antiemetic drugs which are phlogogenic and irritant, for example drugs which are selective serotonin receptor antagonists, such as dolasetron.

Families of bronchodilator drugs which are phlogogenic and irritant, for example methylxanthine drugs, such as aminofilin.

Families of analgesic drugs which are phlogogenic and irritant, for example drugs which are m-receptor agonists, such as morphine.

Families of antiviral drugs which are phlogogenic and irritant, for example drugs which are derived from guanosine, such as aciclovir.

Of course, the device of the invention can advantageously also be used for the endovascular administration of non-cytotoxic therapeutic agents or of any other desired liquid, such as a physiological solution, or a nutritional solution, or a placebo solution or any solution with osmolarity less than 250 mEq/l or greater than 350 mEq/l and/or with a pH less than 7.35 or greater than 7.45.

Furthermore, although the use of autologous blood is preferred as the liquid to be introduced into the collection chamber before introduction of the therapeutic agent, other liquids may also be used, for example heterologous blood, synthetic blood, artificial blood, portions of blood (for example plasma or haematocrit), or else another therapeutic agent or diluting agent depending on the required application.

If necessary, the device of the invention can be provided with a stirrer or can be subjected to stirring via an external stirrer in order to prevent the effect of standstill and stratification caused by the earth's gravitational force, further improving the obtainable mixing effect. The effect of stirring can also be obtained with a bubbler which introduces a flow of inert gas into the collection chamber 11 at the base thereof. In order to avoid overpressure, the inert gas will be discharged, for example via a suitable air vent formed in the vessel.

Some infusion devices according to the invention were subjected to the tests reported hereinafter in order to assess their operation.

EXAMPLE 1

A device according to the first embodiment described above (type 1, cf. FIGS. 1 and 2) having a vessel 10 with maximum useful volume (from the base to the opening 14a of the first outlet duct) of 78 ml was connected to a drip bag containing a solution of 150 ml of 33% glucose monohydrate.

Previously, 39 ml of fresh pig's blood (T<5 h) pre-treated with anticoagulant (trisodium sodium citrate) were introduced into the collection chamber 11 of the vessel 10 so as to obtain a ratio of approximately 1:3.9 between the blood pre-loaded in the vessel 10 and the total glucose solution to be administered.

The flow regulator 18 was then opened so as to allow a flow of glucose solution of 8-10 ml/min from the drip bag to the vessel 10 and from the vessel 10 through the first outlet duct 14, at the outlet of which samples of the mixture were collected at precise and constant intervals of 60 seconds until said mixture had been depleted.

As soon as there was no more glucose solution in the drip bag, the valve 17 was opened immediately in order to allow the vessel 10 to be completely emptied via the second outlet duct 15.

The flow regulator 18 was closed before any air entered the second outlet duct 15.

The samples collected were analysed using a previously calibrated digital refractometer in order to determine their glucose concentration in terms of Brix degrees. The values obtained were recorded in curve A of the graph in FIG. 7 and are commented on below.

The time 0 represents the moment at which the flow regulator 18 was opened; the point a1 indicates the first sample that was collected after the period of time required to fill the vessel 10, the first outlet duct 14 and the test tube for the first sample; point a7 indicates the sample corresponding to emptying of the drip bag 2 and the moment at which the shut-off device 17 was opened; point a15 indicates the sample corresponding to emptying of the device 1.

The administration lasted for a total of approximately 900 seconds, at an average speed of approximately 12 ml/min, which conforms to the requirements of the protocols for administering anhydrous glucose.

Figure 7:
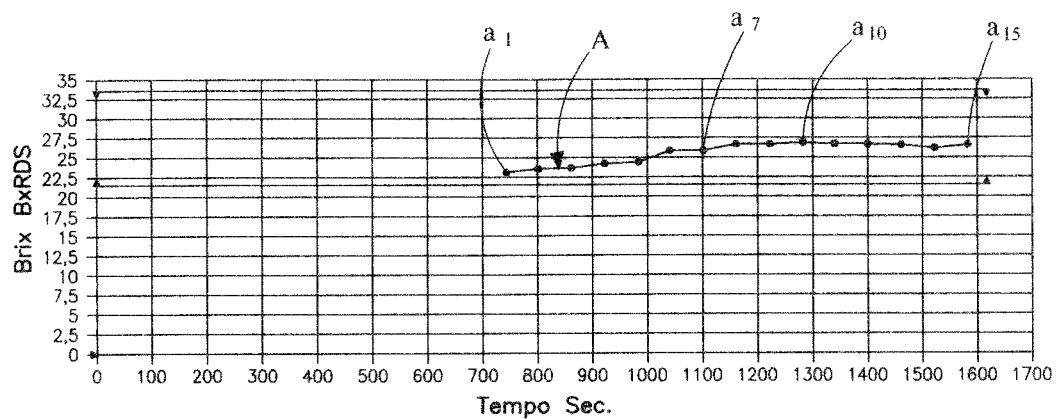
FIGS. 7 to 11 are graphs which show the variation in concentration of a solid solute in a solution exiting a device according to the invention during the administration period.

As can be seen from the graph, throughout the entire administration phase the concentration values of the samples analysed are always less than the maximum concentration of 33% of the glucose solution (represented by the upper line in the graph in FIG. 7), and in fact the average concentration value is 25.35 Brix degrees (with a maximum value of 26.6 Brix degrees, point a10), which is extremely close to the typical concentration of approximately 22 Brix degrees of the pig's blood initially present in the vessel 10 (represented by the lower line in the graph in FIG. 7).

It will be noted that without the device of the invention the patient would be exposed to the high concentration of glucose of 33% for the entire administration period and would therefore be susceptible to the damage caused by the agents used, which have an osmolarity greater than 350 mEq/litre and/or an acidic pH, such as episodes of phlebitis, necrosis, sclerosis, infiltration, ulceration, blistering, phlogosis and thrombosis with all the associated discomfort and risks.

The test therefore shows that it will be possible, with an appropriately dimensioned vessel and with a suitable amount of pre-loaded blood, to avoid the damage caused by solutions of high osmolarity.

EXAMPLE 2

A test similar to Example 1 was carried out using a different blood-glucose ratio.

In particular, the same device as in the example above, into the vessel of which 39 ml of fresh pig's blood (T<5 h) pre-treated with anticoagulant (trisodium sodium citrate) were introduced, was connected to a drip bag containing 78 ml of 33% glucose solution in order to obtain a blood/glucose ratio of 1:2.

Once the flow regulator 18 had been opened, samples of blood/glucose solution mixture were collected and analysed using the same methods as in the example above.

Figure 8:
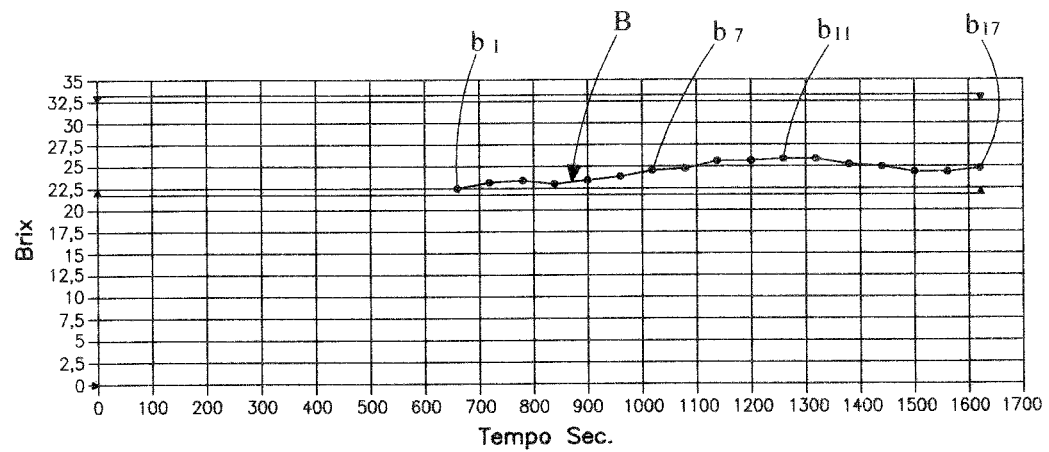

The results of the analyses of the samples collected are reported in curve B of the graph in FIG. 8, where the time 0 represents the moment at which the flow regulator 18 was opened, point b1 represents the first sample that was collected once the vessel 10 and the first outlet duct 14 had been filled, point b7 corresponds to the emptying of the bag 2 and the opening of the shut-off device 17, and point b17 corresponds to the emptying of the vessel 10.

The administration lasted for a total of approximately 1020 seconds, at an average speed of approximately 6.5 ml/min, which conforms to the requirements of the protocols for administering anhydrous glucose.

As can be seen from the graph, throughout the entire administration phase the concentration values of the samples analysed are always less than the maximum concentration of 33% of the glucose solution (represented by the upper line in the graph in FIG. 8), and in fact the average concentration value is 24.20 Brix degrees (with a maximum value of 25.6 Brix degrees, point b11), which is extremely close to the typical concentration of approximately 22 Brix degrees of the pig's blood initially present in the vessel 10 (represented by the lower line in the graph in FIG. 8).

In this case too, without the device of the invention the patient would be exposed to the high concentration of glucose of 33% for the entire administration period and would therefore be susceptible to the damage caused by the agents used which have an osmolarity greater than 350 mEq/litre and/or an acidic pH, such as episodes of phlebitis, necrosis, sclerosis, infiltration, ulceration, blistering, phlogosis and thrombosis with all the associated discomfort and risks.

The test therefore shows that it will be possible, with an appropriately dimensioned vessel and with a suitable amount of preloaded blood, to avoid the damage caused by solutions of high osmolarity.

EXAMPLE 3

In this test the same device was used as in the examples above, which device was connected to a bag containing 150 ml of a 22.1% sucrose solution and into the vessel 10 of which 39 ml of purified water in accordance with the Official Pharmacopoeia were introduced without the addition of solids. In this case, the water/sucrose solution ratio was therefore 1:3.9. The test was carried out similarly to the examples above, with samples of water/sucrose solution mixture collected every 30 seconds and analysed by digital refractometer.

Figure 9:
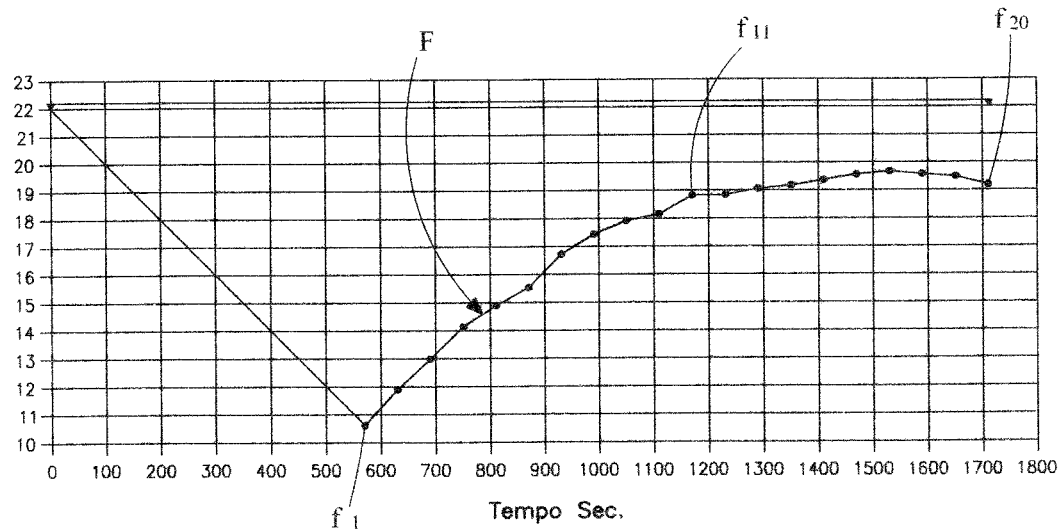

The results of the analyses of the samples collected are reported in curve F of the graph in FIG. 9, where the time 0 represents the moment at which the flow regulator 18 was opened, point f1 represents the first sample that was collected once the vessel 10 and the first outlet duct 14 had been filled, point f11 corresponds to the emptying of the bag 2 and the opening of the shut-off device 17, and point f20 corresponds to the emptying of the vessel 10.

The administration lasted for a total of approximately 1200 seconds, at an average speed of approximately 9 ml/min.

As can be seen from the graph, throughout the entire administration phase the concentration values of the samples analysed are always less than the maximum concentration of the sucrose solution (represented by the upper line in the graph in FIG. 9), with an average concentration value of 17.11 Brix degrees.

EXAMPLE 4

This test was carried out in a manner similar to Example 3, with the difference that the drip bag contained 78 ml of a 5% glucose solution, whereas the vessel 10 was loaded with 39 ml of purified water in accordance with the Official Pharmacopoeia without the addition of solids.

The water/glucose solution ratio was therefore 1:2.

The test was carried out in a manner similar to the examples above, with samples of water/glucose solution mixture collected every 30 seconds and then analysed by digital refractometer.

Figure 10:
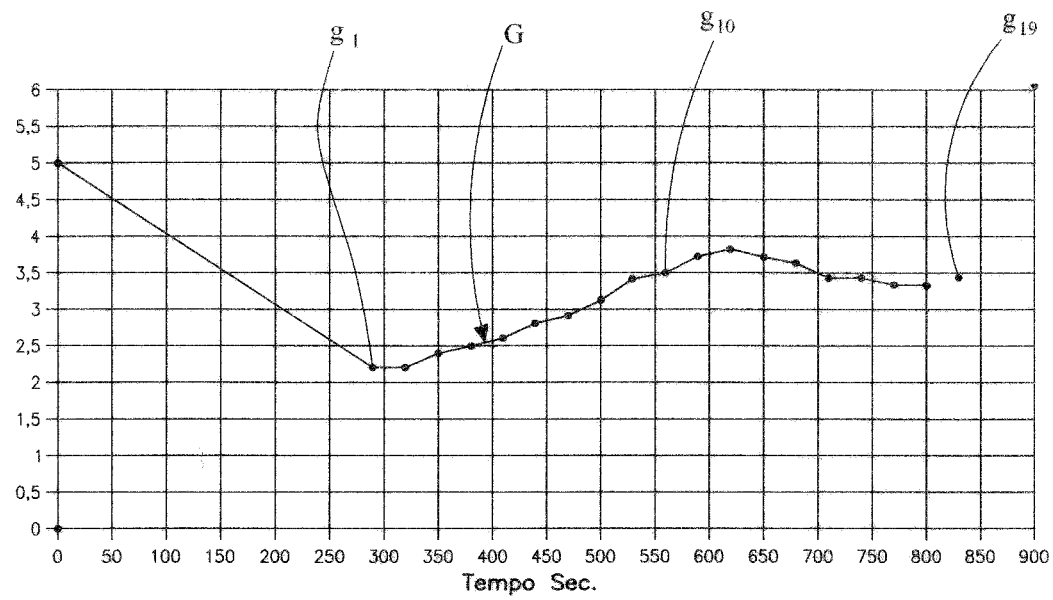

The results of the analyses of the samples collected are reported in curve G of the graph in FIG. 10, where the time 0 represents the moment at which the flow regulator 18 was opened, point g1 represents the first sample that was collected once the vessel 10 and the first outlet duct 14 had been filled, point g10 corresponds to the emptying of the bag 2 and the opening of the shut-off device 17, and point g19 corresponds to the emptying of the vessel 10.

The administration lasted for a total of approximately 600 seconds, at an average speed of approximately 11 ml/min.

As can be seen from the graph, throughout the entire administration phase the concentration values of the samples analysed are always less than the maximum concentration of the glucose solution (represented by the upper line in the graph in FIG. 10), with an average concentration value of 3.12 Brix degrees.

Examples 3 and 4 show how the device 1 is also effective in the mixing of liquids having different densities and chemical-physical properties.

EXAMPLE 5

In this test a device comprising two vessels interconnected in cascade (i.e. in series) was used. In particular, the upstream vessel was constructed similarly to the vessel 10 of the examples described above and the downstream vessel was configured similarly to the vessel 100 of the second embodiment of the invention described above (see FIG. 3). Both the first and second outlet ducts of the upstream vessel 10 were connected to the inlet duct 12 of the downstream vessel 100.

The upstream vessel 10 had a maximum useful volume (as far as the opening 14a) equal to 78 ml, whereas the downstream device 100 had a maximum useful volume of 97 ml.

38 ml and 47.5 ml of purified water were introduced into the vessel 10 and vessel 100 respectively, and the device was then connected to a drip bag containing 150 ml of 15.1% sucrose solution.

The purified water/sucrose solution ratio was thus 1:1.75.

Once the flow regulator had been opened, samples were collected every 60 seconds until the second vessel 100 had been depleted.

Figure 11:
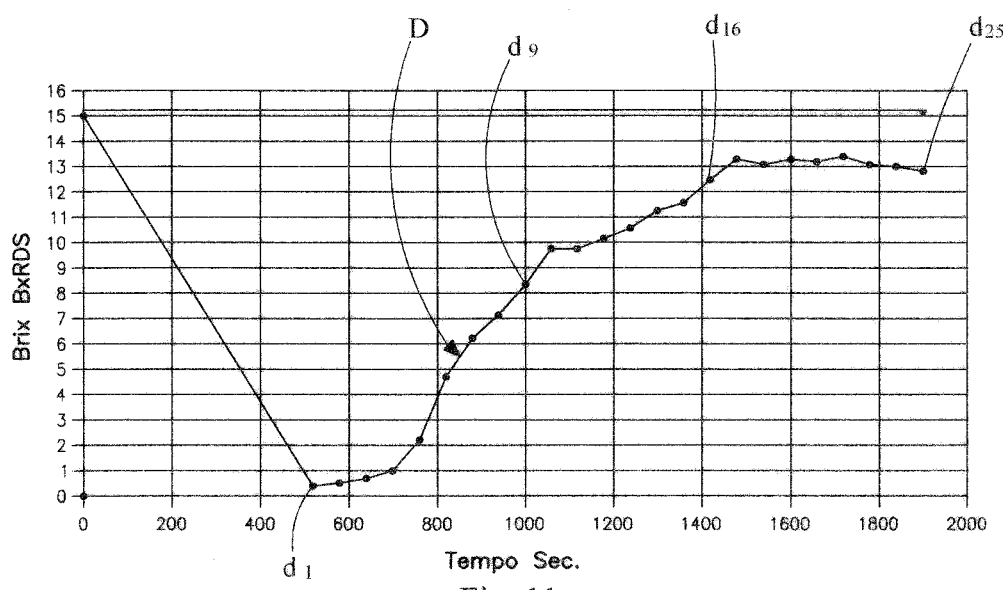

The samples were analysed as in the examples above by digital refractometer and the results are reported in curve D of the graph in FIG. 11, where the time 0 represents the moment at which the flow regulator 18 was opened, point d1 represents the first sample that was collected once the vessels 10 and 100 as well as the respective first outlet ducts had been filled, point d9 corresponds to the emptying of the bag 2 and the opening of the first shut-off means of the first vessel 10, point d16 corresponds to the emptying of the first vessel 10 and the opening of the first shut-off means of the second vessel 100, and point d25 corresponds to the emptying of the vessel 100.

The administration lasted for a total of approximately 1480 seconds, at an average speed of approximately 9.18 ml/min.

As can be seen from the graph, throughout the entire administration phase the concentration values of the samples analysed are always less than the maximum concentration of the sucrose solution (represented by the upper line in the graph in FIG. 11), with an average concentration value of 8.12 Brix degrees and a maximum concentration value of 13.3 Brix degrees.

The invention claimed is:

1. Device for administering liquids to an animal body, in particular therapeutic agents, comprising a vessel defining a collection chamber therein, the following components being provided on said vessel:
   an inlet opening for said therapeutic agent into said collection chamber, and
   a first outlet duct connected to a cannula element which is arranged so as to be introduced into said animal body, the opening of said first outlet duct into said collection chamber being provided at a distance from a base of said vessel,
   wherein a second outlet duct is also provided on said vessel and is connected to a cannula element which is arranged so as to be introduced into said animal body, the opening of said second outlet duct being provided substantially at said base of said vessel, as well as first shut-off device for selectively shutting off said second outlet duct, said first shut-off device being provided for preventing or allowing a flow from said collection chamber through said second outlet duct, wherein said inlet opening is formed in an inlet duct extending inside said collection chamber, and wherein when said vessel is in use said inlet opening is at a level below the opening of said first outlet duct.

2. Device according to claim 1, wherein said opening of said first outlet duct is offset relative to the vertical of said inlet opening.

3. Device according to claim 1, wherein said first outlet duct extends inside said collection chamber along a wall of said vessel.

4. Device according to claim 1, wherein said inlet duct extends inside said collection chamber along a wall of said vessel.

5. Device according to claim 4, wherein said inlet duct extends inside said collection chamber opposite said first outlet duct.

6. Device according to claim 1, wherein said collection chamber has a volume that is defined between said base and a level corresponding to said opening of said first outlet duct and is between 50 and 500 ml.

7. Device according to claim 1, wherein said first compartment and said second compartment are interconnected via a connecting duct.

8. Device according to claim 7, wherein said connecting duct opens into said first compartment at a level above said inlet opening.

9. Device according to claim 7, wherein said connecting duct opens into said second compartment at a level below the opening of said first outlet duct.

10. Device according to claim 1, wherein said cannula element comprises a needle.

11. Device according to claim 1, wherein said cannula element comprises a catheter.

12. Method for diluting a therapeutic agent, comprising the following steps:
    providing a device comprising a vessel defining a collection chamber therein, the following components being provided on said vessel:
    i) an inlet opening for said therapeutic agent into said collection chamber,
    ii) a first outlet duct of which the opening into said collection chamber is arranged at a distance from a base of said vessel,
    iii) a second outlet duct of which the opening is arranged substantially at said base of said vessel, and
    iv) first shut-off means for selectively shutting off said second outlet duct, said first shut-off device being provided for preventing or allowing a flow from said collection chamber through said second duct,
    closing said first shut-off device for shutting off said second outlet duct,
    introducing a predetermined amount of a liquid into said collection chamber,
    adding said therapeutic agent to said collection chamber so it mixes with said liquid, allowing a flow of said mixture of liquid and therapeutic agent from said vessel through said first outlet duct,
    introducing the rest of said therapeutic agent to said collection chamber, the amount of therapeutic agent being provided in accordance with a predetermined flow rate,
    opening said first shut-off device so as to allow said mixture of fluid and therapeutic agent to flow from said second outlet duct.

13. Method according to claim 12, wherein said liquid is introduced into said collection chamber by vacuum suction.

14. Method according to claim 13, wherein said liquid is introduced into said collection chamber by vacuum suction through said first outlet duct.

15. Method according to claim 12, wherein said first opening of said first outlet duct of said device is offset relative to the vertical of said inlet opening.

16. Method according to claim 12, wherein said predetermined amount of said liquid is calculated in such a way that the concentration of the therapeutic agent does not exceed a maximum permitted concentration.

17. Method according to claim 12, wherein after completion of said flow through said second outlet duct a washing phase of said collection chamber takes place using a physiological solution which is flowed through said first and said second outlet ducts.

18. Method according to claim 12, wherein said liquid is autologous blood.

19. Method according to claim 12, wherein said therapeutic agent is a cytotoxic drug.

20. Device for administering liquids to an animal body, in particular therapeutic agents, comprising a vessel defining a collection chamber therein, the following components being provided on said vessel:

an inlet opening for said therapeutic agent into said collection chamber, and a first outlet duct connected to a cannula element which is arranged so as to be introduced into said animal body, an opening of said first outlet duct into said collection chamber being provided at a distance from a base of said vessel, wherein a second outlet duct is also provided on said vessel and is connected to the cannula element which is arranged so as to be introduced into said animal body, and opening of said base of said vessel, as well as a first shut-off device for selectively shutting off said second outlet duct, said first shut-off device being provided for preventing or allowing a flow from said collection chamber through said second outlet duct, wherein said inlet opening is formed in an inlet duct extending inside said collection chamber, and wherein said first outlet duct and said second outlet duct are interconnected downstream of said first shut-off device.

21. Device for administering liquids to an animal body, in particular therapeutic agents, comprising a vessel defining a collection chamber therein, the following components being provided on said vessel:

an inlet opening for said therapeutic agent into said collection chamber, and a first outlet duct connected to a cannula element which is arranged so as to be introduced into said animal body, an opening of said first outlet duct into said collection chamber being provided at a distance from a base of said vessel, wherein a second outlet duct is also provided on said vessel and is connected to the cannula element which is arranged so as to be introduced into said animal body, and opening of said second outlet duct being provided substantially at said base of said vessel, as well as a first shut-off device for selectively shutting off said second outlet duct, said first shut-off device being provided for preventing or allowing a flow from said collection chamber through said second outlet duct, wherein said inlet opening is formed in an inlet duct extending inside said collection chamber, wherein said collection chamber is separated at least into a first compartment and a second compartment in fluid communication with said first compartment and arranged below said first compartment, said inlet opening being provided in said first compartment, wherein said first outlet duct and said second outlet duct open into said second compartment, wherein a third outlet duct for allowing said first compartment to be emptied is provided at a base of said first compartment, wherein said first compartment and said second compartment are interconnected via a connecting duct, and wherein said third outlet duct is connected, downstream of a second shut-off device, to a portion of said connecting duct extending into said second compartment.

22. Device for administering liquids to an animal body, in particular therapeutic agents, comprising a vessel defining a collection chamber therein, the following components being provided on said vessel:

an inlet opening for said therapeutic agent into said collection chamber, and a first outlet duct connected to a cannula element which is arranged so as to be introduced into said animal body, an opening of said first outlet duct into said collection chamber being provided at a distance from a base of said vessel, wherein a second outlet duct is also provided on said vessel and is connected to the cannula element which is arranged so as to be introduced into said animal body, an opening of said second outlet duct being provided substantially at said base of said vessel, as well as a first shut-off device for selectively shutting off said second outlet duct, said first shut-off device being provided for preventing or allowing a flow from said collection chamber through said second outlet duct, wherein said inlet opening is formed in an inlet duct extending inside said collection chamber, wherein said collection chamber is separated at least into a first compartment and a second compartment in fluid communication with said first compartment and arranged below said first compartment, said inlet opening being provided in said first compartment, wherein said first outlet duct and said second outlet duct open into said second compartment, wherein a third outlet duct for allowing said first compartment to be emptied is provided at a base of said first compartment, and wherein said third outlet duct is connected to said second outlet duct upstream of said first shut-off device.

23. Device for administering liquids to an animal body, in particular therapeutic agents, comprising a vessel defining a collection chamber therein, the following components being provided on said vessel:

an inlet opening for said therapeutic agent into said collection chamber, and a first outlet duct connected to a cannula element which is arranged so as to be introduced into said animal body, an opening of said first outlet duct into said collection chamber being provided at a distance from a base of said vessel, wherein a second outlet duct is also provided on said vessel and is connected to the cannula element which is arranged so as to be introduced into said animal body, an opening of said second outlet duct being provided substantially at said base of said vessel, as well as a first shut-off device for selectively shutting off said second outlet duct, said first shut-off device being provided for preventing or allowing a flow from said collection chamber through said second outlet duct, wherein said inlet opening is formed in an inlet duct extending inside said collection chamber, wherein said first outlet duct comprises an ascending branch and a descending branch which are interconnected by a curve of maximum height, wherein said opening of said first outlet duct is formed at a level below said curve of maximum height, and wherein a vent which opens inside said collection chamber at a level above said curve of maximum height is formed on said descending branch.

* * * * *